(12) United States Patent
Taylor

(10) Patent No.: US 8,596,224 B2
(45) Date of Patent: Dec. 3, 2013

(54) ADJUSTABLE MUZZLE

(76) Inventor: Wesley M. Taylor, McKinney, TX (US)

( * ) Notice: Subject to any disclaimer, the term of this patent is extended or adjusted under 35 U.S.C. 154(b) by 295 days.

(21) Appl. No.: 12/927,024

(22) Filed: Nov. 5, 2010

(65) Prior Publication Data

US 2011/0107982 A1    May 12, 2011

Related U.S. Application Data

(60) Provisional application No. 61/280,531, filed on Nov. 6, 2009.

(51) Int. Cl.
    A01K 25/00    (2006.01)
    A61D 7/04    (2006.01)
(52) U.S. Cl.
    USPC ............................................ 119/831; 119/833
(58) Field of Classification Search
    USPC .......................... 119/814, 821, 823, 831–833
    See application file for complete search history.

(56) References Cited

U.S. PATENT DOCUMENTS

| 1,474,303 | A | * | 11/1923 | Joe Veres | 119/831 |
| 4,252,086 | A | * | 2/1981 | Schenck | 119/831 |
| 4,549,501 | A | * | 10/1985 | Anderson et al. | 119/729 |
| 4,603,659 | A | | 8/1986 | Helphry | |
| 5,136,984 | A | * | 8/1992 | Askinasi | 119/831 |
| 5,267,529 | A | * | 12/1993 | Zelinger | 119/831 |
| 5,762,030 | A | * | 6/1998 | Pagliericcio et al. | 119/831 |
| 5,785,008 | A | * | 7/1998 | Liu | 119/831 |
| 5,954,049 | A | * | 9/1999 | Foley et al. | 128/203.29 |
| 6,164,246 | A | * | 12/2000 | Naftaly et al. | 119/720 |
| 6,349,725 | B1 | * | 2/2002 | Perkins et al. | 128/206.21 |
| 7,077,126 | B2 | * | 7/2006 | Kummer et al. | 128/200.23 |
| 7,111,626 | B2 | * | 9/2006 | Schmehl et al. | 128/206.21 |
| 7,891,321 | B2 | * | 2/2011 | Slank | 119/831 |
| 2002/0056456 | A1 | * | 5/2002 | Foley et al. | 128/206.21 |
| 2004/0154622 | A1 | * | 8/2004 | Davis | 128/207.14 |

* cited by examiner

Primary Examiner — David Parsley

(57) ABSTRACT

A muzzle for use with an animal, the muzzle having a muzzle body, at least one strap circumferentially affixed to the muzzle body and adapted to widen or narrow the muzzle body using a tensioning mechanism and a clip coupled to the muzzle body configured to receive an emergency airway device or an endotracheal tube.

6 Claims, 5 Drawing Sheets

ADJUSTABLE MUZZLE

CROSS REFERENCE TO RELATED APPLICATION

This application claims the benefit of U.S. Provisional Application No. 61/280,531, filed on Nov. 6, 2010, entitled "IMPROVED ADJUSTABLE MUZZLE."

TECHNICAL FIELD

The present invention relates to muzzles, for use, for example, by EMT, paramedics, police, military and veterinary personnel for protection during treatment of injured or aggressive dogs and for providing the ability to control the mouth of a dog while retaining the ability to obtain an emergency airway for an injured animal, such as a canine.

BACKGROUND OF THE INVENTION

A muzzle is a device that is typically placed over the snout of an animal to keep it from opening its mouth. They are conventionally made with a strong buckle or other fastening device to ensure that they do not come off accidentally, and are not adjustable. Muzzles are typically made of a durable material that includes air holes to allow the animal to breathe, or formed from a set of straps that provides better air circulation and allow the animal to drink. Leather, wire, plastic, mesh, nylon webbing and woven material are common materials for muzzles. The shape and construction of conventional muzzles might differ depending on whether the intent is to prevent an animal from biting or from eating, for example. A conventional muzzle can be seen at U.S. Pat. No. 4,603,659.

Disadvantageously, conventional muzzles do not have an adjustable muzzle body that can be placed on the snout of the animal in an open position, which provides for easier placement on the animal, and then tightened to restrict the mouth from opening. Also, because conventional muzzles have only one position on the animal's snout after placement, they do not allow for either passage of an emergency airway by opening the muzzle diameter, or increased security by closing the muzzle diameter, or airway retention by clamping the animal's teeth around the airway device. What is desired is a muzzle that includes a muzzle body can be adjusted so as to permit (i) the insertion and removal of a medical device, such as an emergency airway device in an animal, as well as (ii) easier placement of the muzzle in an open position, and (iii) tightening or loosening of the muzzle while still in place on the animal's head.

SUMMARY OF THE INVENTION

A first embodiment of the invention comprises a muzzle having a muzzle body with a generally cone shape having a curved surface area with an open base, and further having a portion thereof, including the apex, removed by taking a flat plane at a right angle to the perpendicular height of the cone a predetermined distance below the apex, thus providing generally a frustum of a cone with a front opening, and being cut along the slant height to create sides, said curved surface area of the muzzle body thus having a front opening and base opening and a left side and right side when viewed into the front opening. Coupled, circumferentially, along the surface of the muzzle body, at least one, and preferably a plurality of, adjustable straps that can be loosened or tightened using tensioning mechanism(s) so as to adjust the relative positions of the sides and also adjusting the size of the front opening of the muzzle body.

A second embodiment of the invention comprises a muzzle having a muzzle body in the shape of a generally oblique circular cone having a curved surface area with an open base, further with a portion thereof, including the apex, removed by taking a flat plane at a right angle to the vertical axis of the cone a predetermined distance below the apex, providing generally a frustum of an oblique circular cone, thus providing a front opening, and further having removed opposite the vertical axis of the generally oblique circular cone, a surface area in the shape of a generally isosceles trapezoid, the unequal sides of the removed, generally isosceles trapezoid portion being a portion of the perimeter of the front opening and a portion of the perimeter of the base opening, the removed portion representing between ⅕ and ½ of the surface area of the generally oblique circular cone, the curved surface area of the muzzle body with the removed portion thus having a left side and right when viewed into the front opening.

The muzzle body further having coupled, circumferentially, along the outside surface of the muzzle body proximate the front opening, at least one fixed strap defining, along with the front opening, an aperture large enough to allow an animal to open its mouth. Further, around the outside of the at least one fixed strap and outside surface of the muzzle body, at least one adjustable strap is coupled to the muzzle body and/or fixed strap, the at least one adjustable strap configured to be loosened or tightened using tensioning mechanism(s) so as to adjust the size of the aperture defined by the front opening and fixed strap of the muzzle body.

To those skilled in the art to which this invention relates, many changes in construction and widely differing embodiments and applications of the invention will suggest themselves without departing from the scope of the invention as defined in the appended claim. The disclosures and the descriptions herein are purely illustrative and are not intended to be in any sense limiting.

BRIEF DESCRIPTION OF THE DRAWINGS

For a better understanding of an embodiment of the invention including the features, advantages and specific embodiments, reference is made to the following detailed description along with accompanying drawings in which.

References in the detailed description correspond to like references in the Figure unless otherwise noted.

DETAILED DESCRIPTION OF A PREFERRED EMBODIMENT

While the making and using of the disclosed embodiments of the present invention is discussed in detail below, it should be appreciated that the present invention provides many applicable inventive concepts which can be embodied in a wide variety of specific contexts.

Some features of the embodiments shown and discussed may be simplified or exaggerated for illustrating the principles of the invention.

Figure 1:
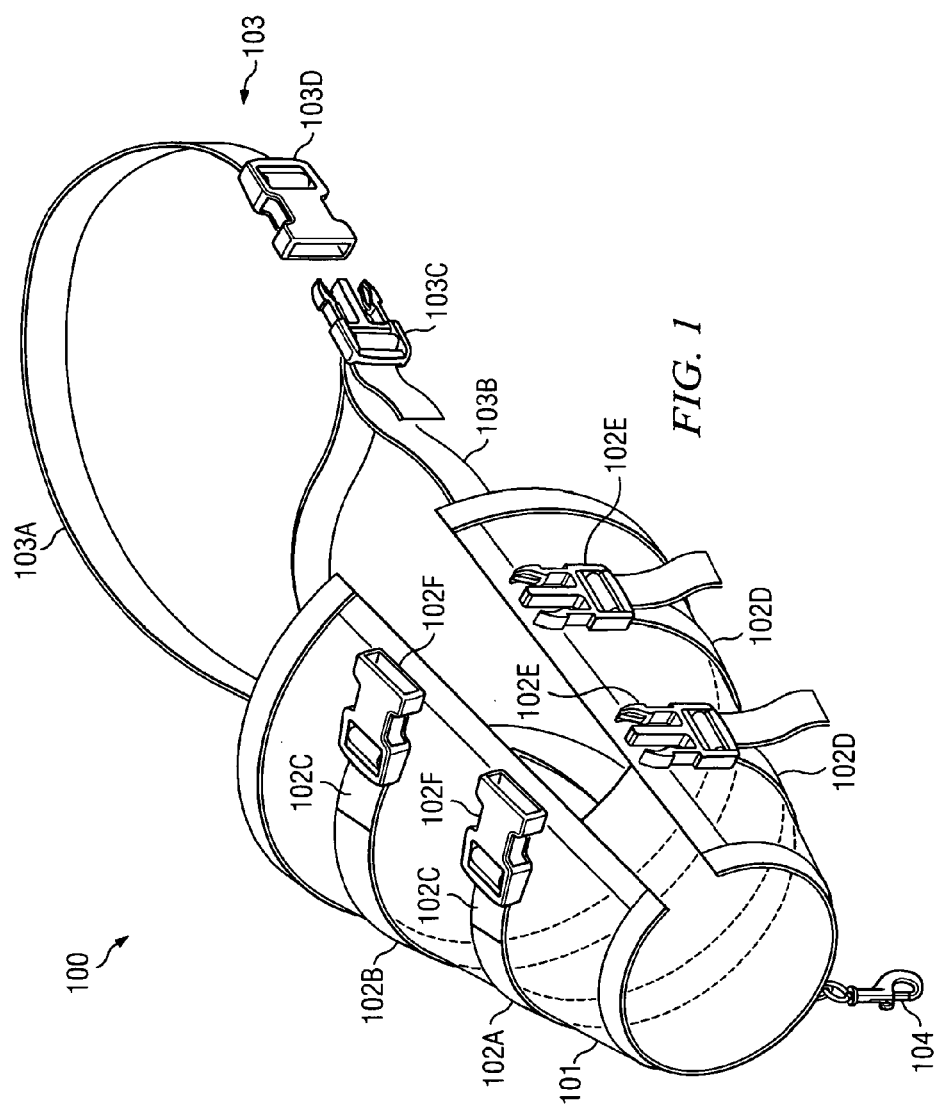
FIG. 1 is a perspective view of a first embodiment of the invention.

Referring to FIG. 1, a first embodiment of the invention comprises a muzzle 100 having a muzzle body 101 having a generally cone shape with a curved surface area with a portion thereof in the shape of a cone, including the apex, removed by taking a flat plane at a right angle to the vertical axis of the cone a predetermined distance below the apex, thus providing generally a frustum of a cone with a front opening and base opening, and having a cut along the slant height defining edges, said muzzle body thus having a front opening and base opening, and when viewed into the front opening, a left side and a right side.

Muzzle body 101 has at least one strap and preferably two or more straps 102A, 102B, as seen in FIG. 1, that are coupled circumferentially to the muzzle body 101. In an aspect of the first embodiment, the straps 102A, 102B are fixedly fastened to the muzzle body 101 by stitching. Each strap 102A, 102B has on each of its ends a strap extension 102C, 102D respectively extended from, and integral with, two opposite ends of straps 102A, 102B, and each strap extension 102C, 102D has a coupling mechanism with an integrated tensioning mechanism. The coupling mechanism comprises a male snap element 102E and a female snap element 102F respectively coupled to the two strap extensions 102C, 102D and is configured to join them. Using the tensioning mechanism, straps 102A, 102B are configured to be loosened or tightened thereby widening or narrowing, respectively, the muzzle body 101 so as to permit the placement and securing of a medical device including but not limited to an emergency airway device and/or an endotracheal tube. The straps are made of a resilient, narrow fabric, such as, but not limited to, polyester, polypropylene, cotton or nylon webbing, or braided, netted or woven elastic. The muzzle body 101 which, when placed on the animal partially to fully surrounds the snout of the animal can be made from any variety of materials, including but not limited to leather, flexible plastic, mesh, nylon webbing and/or woven material.

Longitudinal strap 103 is comprised of a first part 103A, and a second part 103B and a coupling mechanism configured for securing the muzzle body 101 to the head of the animal over its snout and mouth. The first part 103A and second part 103B are each fixedly fastened to the muzzle body 101 by stitching, each having free end pieces respectively extended from and integral with first part 103A and second part 103B, and further includes a coupling mechanism, as seen in FIG. 1 as a male snap element 103C and a female snap element 103D, configured to join the first part 103A and second part 103B of the straps. Clip 104 is fastened to the front of the muzzle body 101 so as to couple the muzzle to an emergency airway device.

Figure 2:
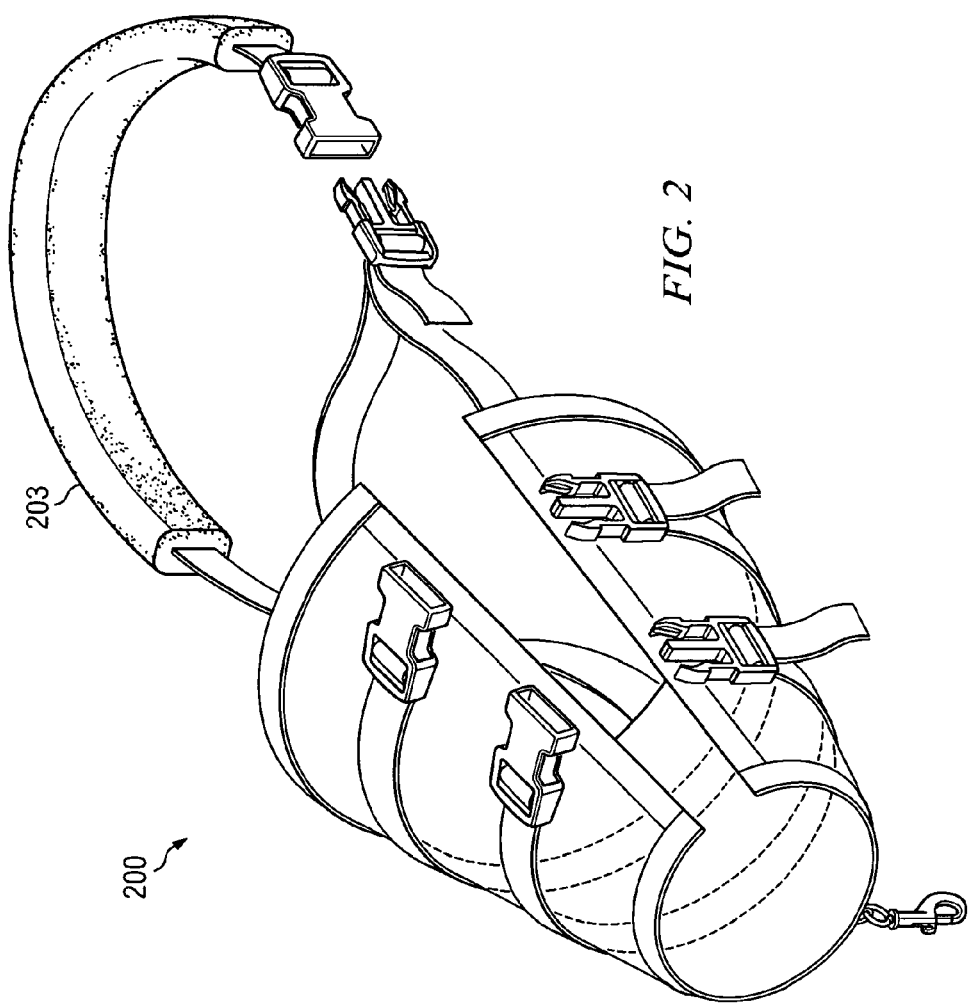
FIG. 2 is a second perspective view of a first embodiment of the invention.

As seen in FIG. 2, muzzle 200 is similar to muzzle 100, however, longitudinal strap 203 is comprised of a thicker material than strap 103. Longitudinal strap 203 can be a thicker portion which integrated to the muzzle 200 or a separate, cushioned portion having an aperture adapted to be slid over strap 103 of FIG. 1. The strap is comprised of a 1" black polypropylene having the following characteristics: warp denier, 1680; binder denier, 840; weft denier, 840; 20 picks/inch; 210-420 lockstitch denier; binder ends, 9; 0.105" to 0.110" thickness with a 1300 lbs minimum tensile strength.

Figure 3:
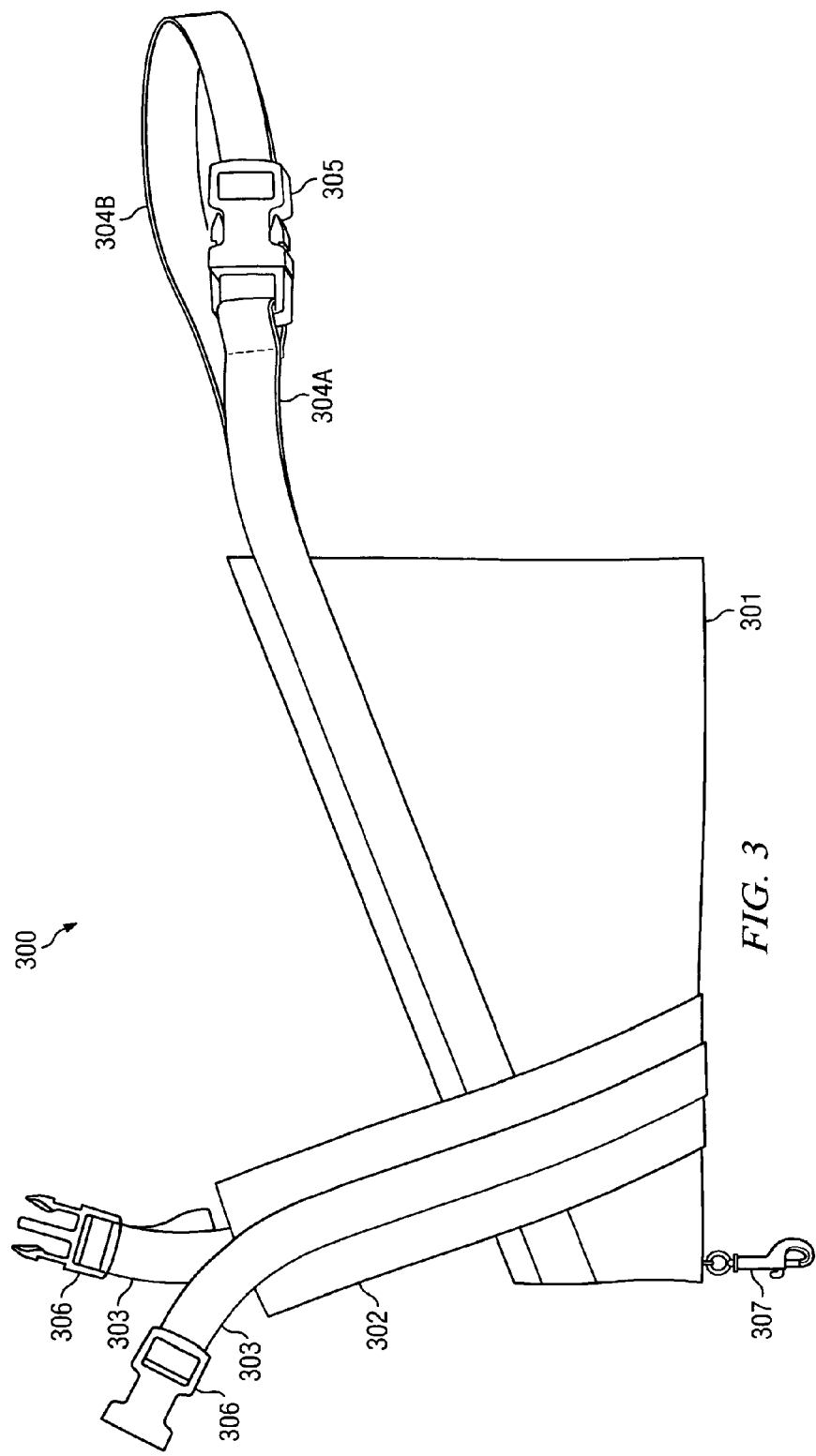
FIG. 3 is a side view of a second embodiment of the invention.

FIG. 3 is a second embodiment of the invention and comprises a muzzle 300 having a muzzle body 301 with a curved surface area in the shape of a generally oblique circular cone having a portion thereof, including the apex, removed by taking a flat plane at a right angle to the vertical axis of the cone a predetermined distance below the apex, thus providing generally a frustum of a oblique circular cone, and further having removed a surface area from the generally oblique circular cone in the shape of a generally isosceles trapezoid portion, the diagonal bisector being opposite the vertical axis of the generally oblique circular cone. The unequal sides of the removed, generally isosceles trapezoid portion are along a portion of the perimeter of the front opening and a portion of the perimeter of the base opening, the removed portion representing between ⅕ and ⅓ of the curved surface area of the generally oblique circular cone.

The muzzle body 301 has coupled, circumferentially, along the outside surface of the muzzle body 301, at least one fixed strap 302 fixedly coupled to the sides of the muzzle body, defining, along with a circumferentially portion of the muzzle body, an aperture large enough to allow an animal on which it is placed to open its mouth. Around the outside of the at least one fixed strap and outside surface of the muzzle body, at least one adjustable strap 303 is coupled to the muzzle body 301 and/or fixed strap 302. The at least one adjustable strap 303 has a coupling mechanism 306 that is configured to be loosened or tightened using tensioning mechanism(s) so as to adjust the size of the aperture defined by the front opening of muzzle body 301 and fixed strap 302. A pair of longitudinal straps 304A, 304B extend along the sides of muzzle body 301 and are joined with a coupling mechanism 305, the pair of longitudinal strap operable to fit around the back of the head of the animal to hold the muzzle 300 in place. Longitudinal straps 304A, 304B can further include a thicker portion which integrated to the muzzle 300 or a separate, cushioned portion having an aperture adapted to be slid over strap 304A, 304B as seen in FIG. 2. Clip 307 is fastened to the front of the muzzle body 301 so as to couple an emergency airway device to the muzzle 300.

Figure 4:
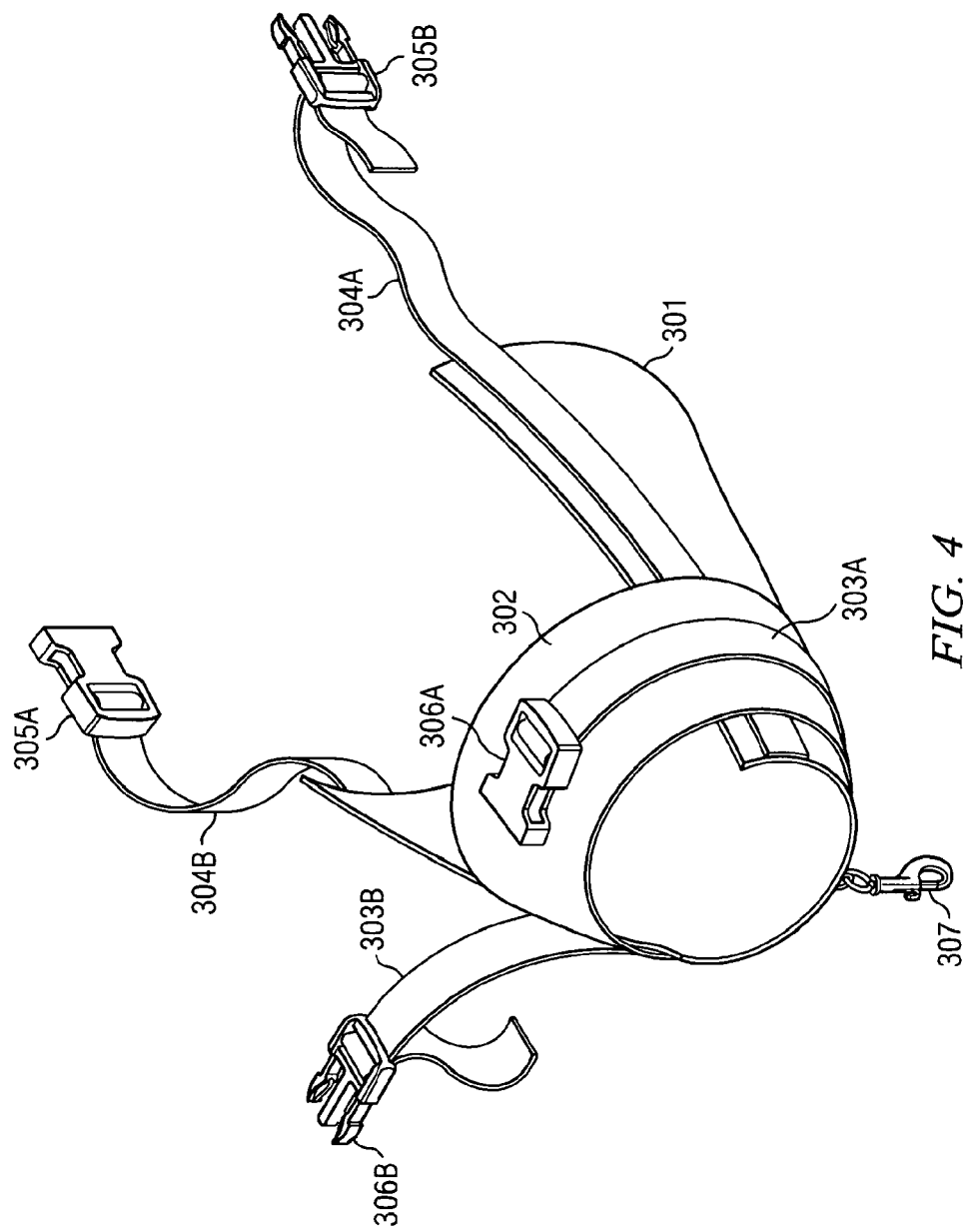
FIG. 4 is a perspective view of a second embodiment of the invention.

FIG. 4 is a perspective view of the second embodiment. As further seen therein, coupled, circumferentially, along the outside surface of the muzzle body 301 proximate the front opening is at least one fixed strap 302, defining, with the front opening, an aperture large enough to allow an animal on which it is placed to open its mouth, and around the outside of the at least one fixed strap and outside surface of the muzzle body, at least adjustable straps 303A, 303B, having coupling mechanism 306A, 306B. In an aspect of the second embodiment, fixed strap 302 is fixedly fastened to the muzzle body by stitching. A first end of straps 303A, 303B are fixedly fastened to fixed strap 302 and/or the muzzle body 301 by stitching. Alternatively, strap 303 can be a single, open ended strap surrounding the outer surface of the fixed strap. Each strap 303A, 303B, or the end of single open ended strap 303, has on its distal ends a coupling mechanism with an integrated tensioning mechanism. The coupling mechanism can include, but is not limited to, a female snap element 306A and a male snap element 306B respectively coupled to the two strap extensions 302A, 302B and is configured to join them. Using the tensioning mechanism, fixed strap 302 is configured to be loosened or tightened thereby widening or narrowing, respectively, the muzzle body 301 so as to permit the placement and securing of a medical device, such as, but not limited to an emergency airway device and/or an endotracheal tube. The straps are made of a resilient, narrow fabric, such as, but not limited to, polyester, polypropylene, cotton or nylon webbing, or braided, netted or woven elastic. The muzzle body 301 which substantially surrounds the snout of the animal can be made from any variety of materials, including but not limited to leather, flexible plastic, mesh, nylon webbing and/or woven material.

Longitudinal strap 304 is comprised of a first part 304A, and a second part 304B and coupling mechanism 305A, 305B configured for securing the muzzle body 301 to the head of the animal over its snout and mouth. The first part 304A and second part 304B are each fixedly fastened to the muzzle body 301 by stitching, each having free end portions respectively extended from the muzzle body 301, and further includes a coupling mechanism 305A, 305B comprising a female snap element 305A and a male snap element 305B, configured to join the first part 304A and second part 304B of the straps.

Figure 5:
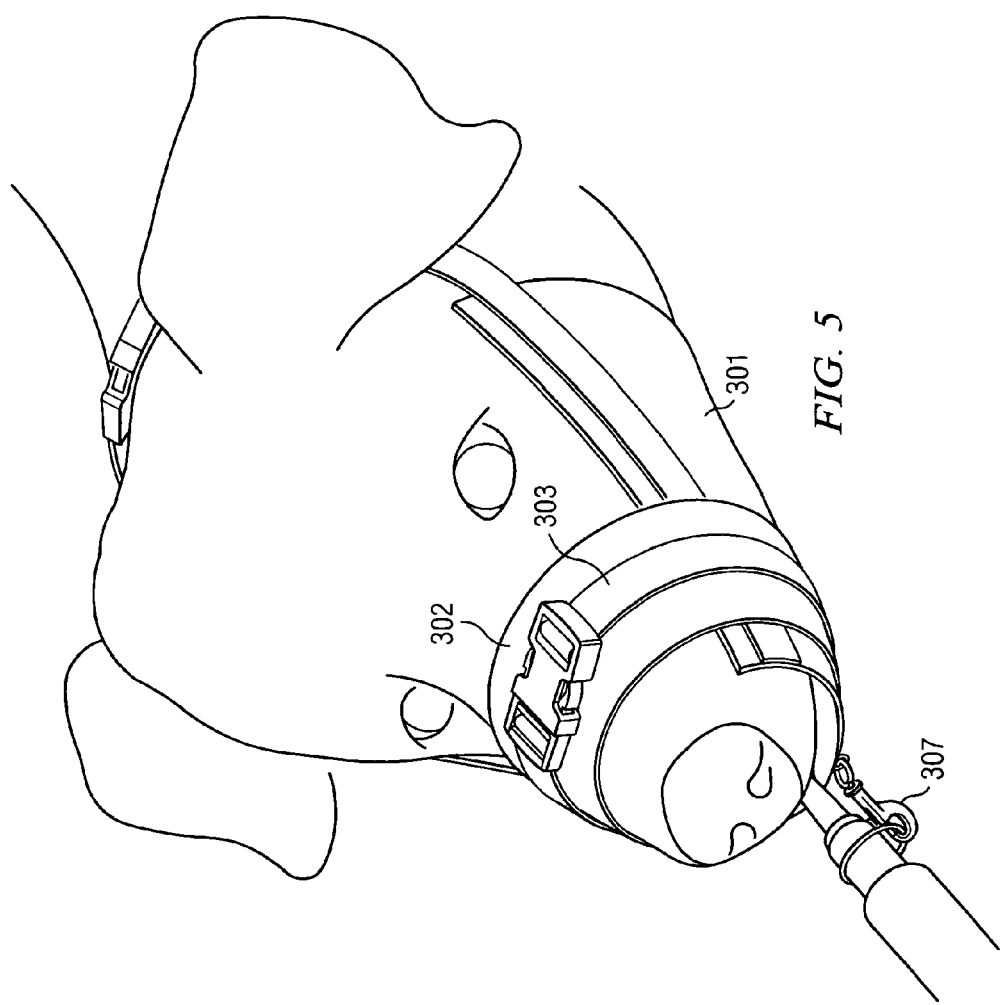
FIG. 5 is a view of a second embodiment of the invention on the snout of an animal.

FIG. 5 illustrates the use of the second embodiment of muzzle 300 on an animal, with an airway tube coupled to muzzle body 301 being fastened to clip 307 and with the fixed strap 302 being tightened around the snout of the animal using adjustable strap 303.

The embodiments shown and described herein are only exemplary. Even though characteristics and advantages of the present invention have been set forth in the foregoing description together with details of embodiments of the invention, the disclosure is illustrative only and changes may be made within the principles of the invention to the full extent indicated by the broad general meaning of the terms used in the attached claims.

What is claimed is:

1. A muzzle, comprising:

a muzzle body having a generally curved surface area in the shape of a generally oblique circular cone with a portion thereof, including the apex, removed by taking a flat plane at a right angle to the vertical axis of the cone a predetermined distance below the apex, providing generally a frustum of an oblique circular cone, and further having removed from the generally oblique circular cone a surface area in the shape of a generally isosceles trapezoid, the diagonal bisector of the removed portion being opposite the vertical axis of the generally oblique circular cone surface, the unequal sides of the removed generally isosceles trapezoid portion being a portion of a perimeter of the front opening and a portion of a perimeter of the base opening, the removed portion representing between $1/5$ and $2/3$ of the surface area of the generally oblique circular cone;

two adjustable, then lockable, straps coupled, circumferentially, around the outside surface of the muzzle body proximate the front opening, the at least one fixed strap defining an aperture large enough to allow an animal on which it is placed to open its mouth;

at least one adjustable strap coupled, circumferentially, around the at least one fixed strap and muzzle body, the at least one adjustable strap configured to be loosened or tightened using tensioning mechanism(s) so as to adjust the size of the aperture defined by the front opening and fixed strap of the muzzle body;

a medical airway clip coupled to the muzzle body for receiving a medical airway device; and a medical airway device coupled to the medical airway clip.

2. The muzzle of claim 1, wherein the medical airway device is an endotracheal tube.

3. The muzzle of claim 1, further comprising an adjustable longitudinal strap for securing the muzzle body to the head of an animal.

4. The muzzle of claim 3, further comprising a cushioned portion positioned over the adjustable longitudinal strap.

5. The muzzle of claim 4, wherein the straps are made from a material selected from the group consisting of polyester, polypropylene, cotton webbing, nylon webbing, braided elastic, netted elastic and woven elastic.

6. The muzzle of claim 1, wherein the muzzle body is made from a material selected from the group consisting of leather, flexible plastic, mesh and nylon.

\* \* \* \* \*